US011898936B2

(12) United States Patent
Fu et al.

(10) Patent No.: US 11,898,936 B2
(45) Date of Patent: Feb. 13, 2024

(54) METHOD AND APPARATUS FOR EVALUATING BODY FEELING OF VEHICLE, ELECTRONIC DEVICE AND STORAGE MEDIUM

(71) Applicant: BEIJING BAIDU NETCOM SCIENCE AND TECHNOLOGY CO., LTD., Beijing (CN)

(72) Inventors: Yiqun Fu, Beijing (CN); Qingyu Li, Beijing (CN); Shengzhao Tao, Beijing (CN)

(73) Assignee: BEIJING BAIDU NETCOM SCIENCE AND TECHNOLOGY CO., LTD., Beijing (CN)

( * ) Notice: Subject to any disclaimer, the term of this patent is extended or adjusted under 35 U.S.C. 154(b) by 290 days.

(21) Appl. No.: 17/215,628

(22) Filed: Mar. 29, 2021

(65) Prior Publication Data
US 2021/0231532 A1 Jul. 29, 2021

(30) Foreign Application Priority Data

May 20, 2020 (CN) .......................... 202010431715.8

(51) Int. Cl.
*G01M 17/04* (2006.01)
*G01M 17/007* (2006.01)

(52) U.S. Cl.
CPC .......... *G01M 17/04* (2013.01); *G01M 17/007* (2013.01)

(58) Field of Classification Search
CPC .... A61B 2562/0219; A61B 2562/0247; A61B 5/1036; A61B 5/18; A61B 5/6893; G01M 17/007; G01M 17/04
See application file for complete search history.

(56) References Cited

U.S. PATENT DOCUMENTS

2012/0253233 A1* 10/2012 Greene .................. G16H 50/30
600/592

FOREIGN PATENT DOCUMENTS

| CN | 106556521 A | 4/2017 |
| CN | 110441048 A | 11/2019 |

(Continued)

OTHER PUBLICATIONS

Tan, Subjective and Objective Measurements for Comfortable Truck Driver's Seat, AVEC '08-141 (Year: 2008).*

(Continued)

*Primary Examiner* — Michael J Dalbo
(74) *Attorney, Agent, or Firm* — Kilpatrick Townsend & Stockton LLP

(57) ABSTRACT

A method and apparatus for evaluating a body feeling of a vehicle, an electronic device and a storage medium are provided. The method includes: a pressure of a measured object acting on each measurement region of a target riding apparatus under a current weight is measured by at least one pressure sensing unit within a measurement time period; a pressure intensity generated by the pressure of the measured object acting on each measurement region is calculated according to the pressure on each measurement region measured by each pressure sensing unit and an individual size of each pressure sensing unit; an objective body feeling evaluation score of the measured object under the current weight is determined according to the measured pressure and the calculated pressure intensity; and a comprehensive body feeling evaluation score is calculated according to the objective body feeling evaluation score and a predetermined subjective body feeling evaluation score.

13 Claims, 5 Drawing Sheets

(56) References Cited

FOREIGN PATENT DOCUMENTS

| | | | |
|---|---|---|---|
| DE | 102018128138 A1 | * | 5/2020 |
| JP | H09-218115 A | | 8/1997 |
| JP | 2018-165070 A | | 10/2018 |
| JP | 2019-202778 A | | 11/2019 |
| JP | 2001-74592 A | | 3/2021 |

OTHER PUBLICATIONS

Kyung, Gyouhyung, et al., "Driver sitting comfort and discomfort (part II): Relationships with and prediction from interface pressure," International Journal of Industrial Ergonomics, Elsevier, Amsterdam, NL, vol. 38, No. 5-6, pp. 526-538, ISSN: 0169-8141, (May 1, 2008).

European Search Report dated Sep. 23, 2021 of the corresponding European Patent Application No. 21165932.1 (35 pages).

* cited by examiner

METHOD AND APPARATUS FOR EVALUATING BODY FEELING OF VEHICLE, ELECTRONIC DEVICE AND STORAGE MEDIUM

CROSS-REFERENCE TO RELATED APPLICATIONS

This application claims priority to Chinese Application No. 202010431715.8, filed on May 20, 2020 and entitled "Method and Apparatus for Evaluating Body Feeling of Vehicle, Electronic Device and Storage Medium," the content of which is hereby incorporated by reference in its entirety.

TECHNICAL FIELD

Embodiments of the present disclosure relate to the field of artificial intelligence, specifically relate to the field of autonomous driving technology, and more specifically to a method and apparatus for evaluating a body feeling of a vehicle, an electronic device and a storage medium.

BACKGROUND

An autonomous vehicle is a kind of intelligent vehicle, can also be referred to as a wheeled mobile robot, and mainly relies on an intelligent pilot based on a computer system in the vehicle to realize autonomous driving. One goal of the autonomous vehicle is to make passengers feel better when riding. In the process of research, development and test of autonomous driving, the feelings of passengers need to be frequently evaluated during the driving process of the vehicle to verify whether the planning of the vehicle needs improvement. Therefore, the effectiveness and efficiency of body feeling evaluation are crucial to the research and development of the autonomous driving.

At present, the body feeling evaluation of autonomous driving in the industry is mainly based on a method of subjective evaluation, so the evaluation results are subjectively affected. During the body feeling evaluation, since the human body feeling tolerance increases with repeated tests, the accuracy of the evaluation results may gradually decrease and the evaluation results are difficult to quantify.

SUMMARY

Embodiments of the present disclosure provide a method and apparatus for evaluating a body feeling of a vehicle, an electronic device and a storage medium, which can improve the accuracy of body feeling evaluation, reduce the one-sidedness of subjective evaluation, and can also obtain quantified results of body feeling measurement.

In a first aspect, an embodiment of the present disclosure provides a method for evaluating a body feeling of a vehicle, the method including: measuring, during a driving process of the vehicle, a pressure of a measured object acting on each measurement region of a target riding apparatus under a current weight through at least one preset pressure sensing unit within a measurement time period; calculating a pressure intensity generated by the pressure of the measured object acting on each measurement region according to the pressure on each measurement region measured by each pressure sensing unit and a predetermined individual size of each pressure sensing unit; determining an objective body feeling evaluation score of the measured object under the current weight according to the measured pressure acting on each measurement region and the calculated pressure intensity generated by the pressure acting on each measurement region; and calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period.

In a second aspect, an embodiment of the present disclosure provides an apparatus for evaluating a body feeling of a vehicle, the apparatus including: a measurement module, a calculation module, an objective body feeling evaluation module, and a comprehensive body feeling evaluation module; where the measurement module is configured to measure, during a driving process of the vehicle, a pressure of a measured object acting on each measurement region of a target riding apparatus under a current weight through at least one preset pressure sensing unit within a measurement time period; the calculation module is configured to calculate a pressure intensity generated by the pressure of the measured object acting on each measurement region according to the pressure on each measurement region measured by each pressure sensing unit and a predetermined individual size of each pressure sensing unit; the objective body feeling evaluation module is configured to determine an objective body feeling evaluation score of the measured object under the current weight according to the measured pressure acting on each measurement region and the calculated pressure intensity generated by the pressure acting on each measurement region; and the comprehensive body feeling evaluation module is configured to calculate a comprehensive body feeling evaluation score of the vehicle driving within the measurement time period according to the objective body feeling evaluation score of the measured object under the current weight and a predetermined subjective body feeling evaluation score of the vehicle driving within the measurement time period.

In a third aspect, an embodiment of the present disclosure provides an electronic device, the device electronic including: one or more processors; and a memory for storing one or more programs, and the one or more programs, when executed by the one or more processors, causing the one or more processors to implement the method for evaluating a body feeling of a vehicle according to any embodiment of the present disclosure.

In a fourth aspect, an embodiment of the present disclosure provides a storage medium storing a computer program thereon, and the program, when executed by a processor, implementing the method for evaluating a body feeling of a vehicle according to any embodiment of the present disclosure.

It should be understood that the content described in this section is neither intended to identify key or important features of embodiments of the present disclosure, nor intended to limit the scope of the present disclosure. Other features of the present disclosure will become readily understood in conjunction with the following description.

BRIEF DESCRIPTION OF THE DRAWINGS

The accompanying drawings are used to better understand the solution and do not constitute limitations to the present disclosure.

DETAILED DESCRIPTION OF EMBODIMENTS

Example embodiments of the present disclosure are described below with reference to the accompanying drawings, including various details of embodiments of the present disclosure to contribute to understanding, which should be considered merely as examples. Therefore, those of ordinary skills in the art should realize that various alterations and modifications can be made to embodiments described here without departing from the scope and spirit of the present disclosure. Similarly, for clarity and conciseness, descriptions of well-known functions and structures are omitted in the following description.

The technology of embodiments of the present disclosure solves the technical problems in the existing technology that the evaluation results are subjectively affected and the body feeling evaluation is inaccurate and difficult to quantify. The technical solution provided in embodiments of the present disclosure can improve the accuracy of body feeling evaluation, reduce the one-sidedness of subjective evaluation, and can also obtain quantified results of body feeling measurement.

First Embodiment

Figure 1:
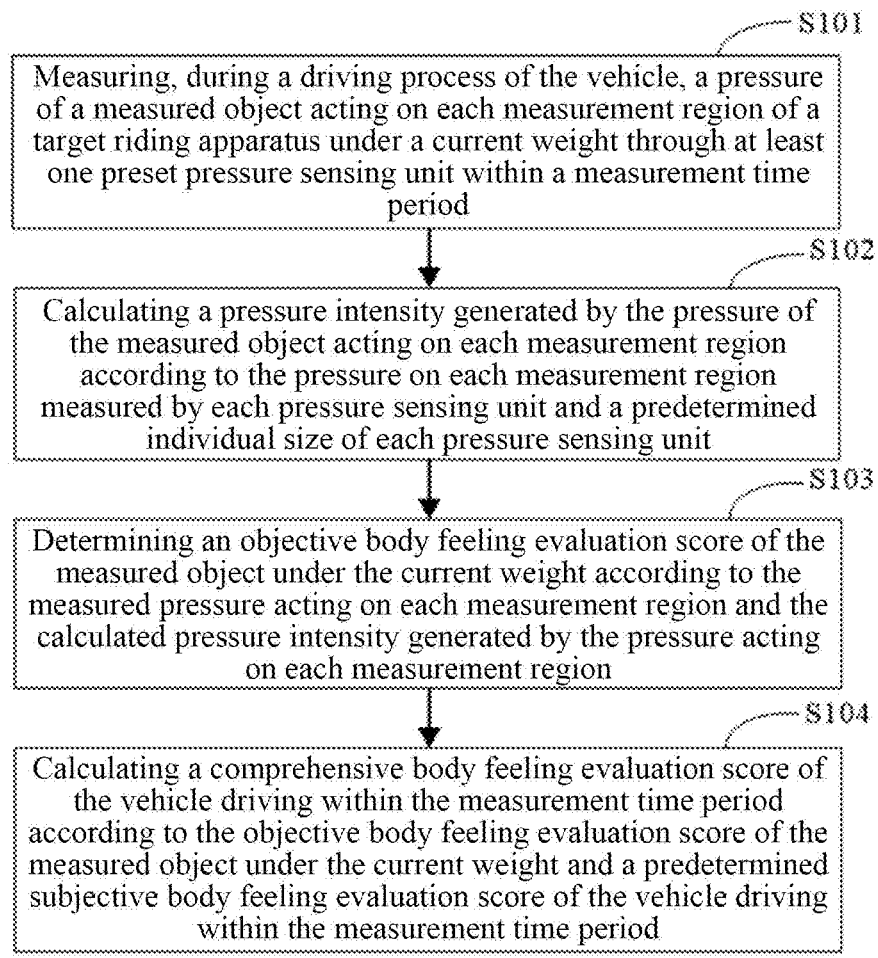
FIG. 1 is a schematic flowchart of a method for evaluating a body feeling of a vehicle according to a first embodiment of the present disclosure.

FIG. 1 is a schematic flowchart of a method for evaluating a body feeling of a vehicle according to the first embodiment of the present disclosure. The method may be executed by an apparatus for evaluating a body feeling of a vehicle or an electronic device. The apparatus or the electronic device may be implemented by means of software and/or hardware, and the apparatus or the electronic device may be integrated in any intelligent device with a network communication function. As shown in FIG. 1, a method for evaluating a body feeling of a vehicle may include the following steps.

S101: measuring, during a driving process of the vehicle, a pressure of a measured object acting on each measurement region of a target riding apparatus under a current weight through at least one preset pressure sensing unit within a measurement time period.

The autonomous driving process of the vehicle may be divided into three stages: start, driving, and stop, and the three stages may also be subdivided. The start stage may be divided into straight, curve, ramp, and follow starts according to scenarios. The driving stage may be discussed from simple to complex due to various behaviors of autonomous driving, and main behaviors may be abstracted from the scenarios. On a simple straight road, the autonomous vehicle may cruise and follow, which require separate body feeling evaluations. The body feeling evaluations are also required for left and right turning scenarios and U-turn scenarios, respectively. In view of the impact of an obstacle on the autonomous vehicle, an intelligent obstacle avoidance behavior needs to be evaluated separately to evaluate the behavior of driving in under continuous traffic flow. In addition, regardless of obstacles, the autonomous vehicle has lane changing behaviors. Further, there may be various traffic signs on the road, such as speed bumps, stop yield signs, and deceleration yield signs that have a great impact on body feeling. For the stop stage, the autonomous vehicle has several situations such as sideways stop, curve stop, ramp stop and follow stop, and the automatic parking function also needs to be considered accordingly. According to the above analysis, the specific scenarios that are more likely to cause body feeling discomfort during the driving process of the vehicle may be shown in Table 1 below:

TABLE 1

| Driving behaviors | Specific scenarios |
| --- | --- |
| Start | Straight start or curve start or ramp start or follow start |
| Cruise | Cruise mode or recognizing a speed limit sign |
| Follow | Emergency brake or acceleration of a target vehicle |
| Left and right turn | Left and right turn at an obstacle-free intersection or left and right turn at an intersection when encountering a target vehicle |
| U-turn | U-turn at an intersection or a straight road or a narrow road |
| Intelligent obstacle avoidance | Pedestrian crossing or target vehicle driving in |
| Merging into traffic | Merging into intensive traffic |
| Lane change | Lane change at a maximum speed or static start or a curve road |
| Passing a speed bump | Single speed bump or continuous speed bumps |
| Passing a yield sign | Stop to yield or slow down to yield |
| Stop | Sideways stop, curve stop, ramp stop, intersection stop or follow stop |
| Automatic parking | Park in a parking space parallel with another parking space, or park in a "side position" or "slash" parking space |

For the 12 driving behaviors in Table 1 that are more likely to cause body feeling discomfort, the body feeling can be evaluated for each specific scenario in the driving behaviors by using the method for evaluating a body feeling of a vehicle according to embodiments of the present disclosure to obtain more accurate, fair and objective evaluations on the comfort level of the autonomous vehicle. Meanwhile, the body feeling evaluation scores of the autonomous vehicle can be used as an important reference for the improvement of the autonomous vehicle.

In this step, during the driving process of the vehicle, the electronic device may measure the pressure, acting on each measurement region of the target riding apparatus, of the measured object under the current weight through at least one preset pressure sensing unit within the measurement time period. The measured object in embodiments of the present disclosure may be a real passenger or a passenger model equivalent to the weight of an adult. When the passenger model is used as the measured object, the weight of the passenger model may be adjusted by adding or releasing liquid in the model. Therefore, when the measured object is under different weights, different objective body feeling evaluation scores may be calculated using the same method, and a change curve of the objective body feeling evaluation scores of the measured object under different weights can be drawn.

In a specific embodiment of the present disclosure, the target riding apparatus may be a seat on which the measured object sits when riding, including the following seat units: a headrest, a backrest, a seat cushion and armrests. Therefore, at least one pressure sensing unit may be arranged on only one or a few of the seat units, or at least one pressure sensing unit may be arranged on each seat unit, which is not limited here.

Figure 2:
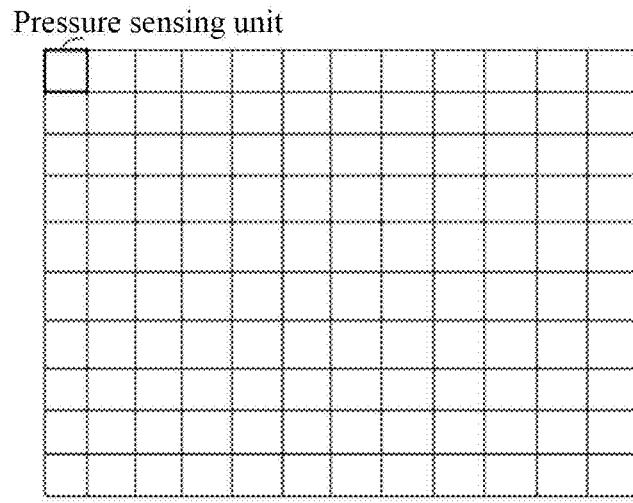
FIG. 2 is a schematic structural diagram of pressure sensing units according to the first embodiment of the present disclosure.

In a specific embodiment of the present disclosure, the pressure sensing unit may be a single pressure sensor, or may be a sensing unit in a pressure sensor. FIG. 2 is a schematic structural diagram of pressure sensing units according to the first embodiment of the present disclosure. As shown in FIG. 2, embodiments of the present disclosure may use each sensing unit in an array pressure sensor as a pressure sensing unit. The array pressure sensor is provided with a plurality of pressure sensing units in the horizontal direction and the vertical direction, and each small square in FIG. 2 represents a pressure sensing unit. Taking the array pressure sensor of model LX210:48.48.02 as an example, the individual size of each pressure sensing unit in this array pressure sensor is 12.7 mm, the sensing area is 60.9 cm×60.9 cm, the measured pressure intensity range is 0.07-10.3 N/cm$^2$, and the array pressure sensor has good flexibility and durability. Since the individual area of the sensor is constant, the pressure intensity measured by the sensor can reflect the force applied by the human body. During pressure measurement, the array pressure sensor may be placed on the seat cushion of the vehicle to record corresponding sensor pressure values when evaluating for each scenario.

S102: calculating a pressure intensity generated by the pressure of the measured object acting on each measurement region according to the pressure on each measurement region measured by each pressure sensing unit and a predetermined individual size of each pressure sensing unit.

In this step, the electronic device may calculate the pressure intensity generated by the pressure of the measured object acting on each measurement region according to the pressure on each measurement region measured by each pressure sensing unit and the predetermined individual size of each pressure sensing unit. Specifically, each pressure sensing unit may measure, in its corresponding measurement region, a pressure of the measured object on the measurement region; and then calculate a pressure intensity generated by the pressure of the measured object on the measurement region by means of the following equation:

$$P = \frac{F}{S};$$

where F represents the pressure of the measured object measured by the current pressure sensing unit on the corresponding measurement region; S represents a force area of the current pressure sensor; and P represents the pressure intensity generated by the pressure of the measured object on the measurement region.

S103: determining an objective body feeling evaluation score of the measured object under the current weight according to the measured pressure acting on each measurement region and the calculated pressure intensity generated by the pressure acting on each measurement region.

In this step, the electronic device may determine the objective body feeling evaluation score of the measured object under the current weight according to the measured pressure acting on each measurement region and the calculated pressure intensity generated by the pressure acting on each measurement region. Specifically, the electronic device may determine the objective body feeling evaluation score of the measured object under the current weight according to the measured pressure acting on each measurement region and a predetermined pressure evaluation weight value, and the calculated pressure intensity generated by the pressure acting on each measurement region and a predetermined pressure intensity evaluation weight value.

S104: calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period.

In this step, the electronic device may calculate the comprehensive body feeling evaluation score of the vehicle driving within the measurement time period according to the objective body feeling evaluation score of the measured object under the current weight and the predetermined subjective body feeling evaluation score of the vehicle driving within the measurement time period. Specifically, the electronic device may calculate a statistical value of the objective body feeling evaluation score of the measured object under the current weight and the predetermined subjective body feeling evaluation score of the vehicle driving within the measurement time period as the comprehensive body feeling evaluation score of the vehicle driving within the measurement time period. For example, the statistical value may include a mean square error or a standard deviation.

In the method for evaluating a body feeling of a vehicle according to embodiments of the present disclosure, a pressure of a measured object acting on each measurement region of a target riding apparatus under a current weight is first measured by at least one pressure sensing unit within a measurement time period; then, a pressure intensity generated by the pressure of the measured object acting on each measurement region is calculated according to the pressure on each measurement region measured by each pressure sensing unit and an individual size of each pressure sensing unit; next, an objective body feeling evaluation score of the measured object under the current weight is determined according to the measured pressure acting on each measurement region and the calculated pressure intensity generated by the pressure acting on each measurement region; and finally, a comprehensive body feeling evaluation score of the vehicle driving within the measurement time period is calculated according to the objective body feeling evaluation score of the measured object under the current weight and a predetermined subjective body feeling evaluation score of the vehicle driving within the measurement time period. That is to say, embodiments of the present disclosure may determine the objective body feeling evaluation score of the measured object under the current weight by means of measuring pressure values through the pressure sensing units, and the score does not rely on the subjective feeling of the passenger and can relatively objectively evaluate the riding experience of the vehicle. The existing method for evaluating a body feeling of a vehicle is mainly based on a method of subjective evaluation, so the evaluation result is subjectively affected. Because embodiments of the present disclosure use the technical means of measuring the pressure on each measurement region through at least one pressure sensing unit during the driving process of the vehicle, the technical problems in the existing technology that the body feeling evaluation is inaccurate and difficult to quantify are overcome. The technical solution provided in embodiments of the present disclosure can improve the accuracy of body feeling evaluation, reduce the one-sidedness of subjective evaluation, and obtain the quantified result of the body feeling measurement. In addition, the technical solution of embodiments of the present disclosure is simple and convenient to implement and easy to popularize, and has a wider application range.

Second Embodiment

Figure 3:
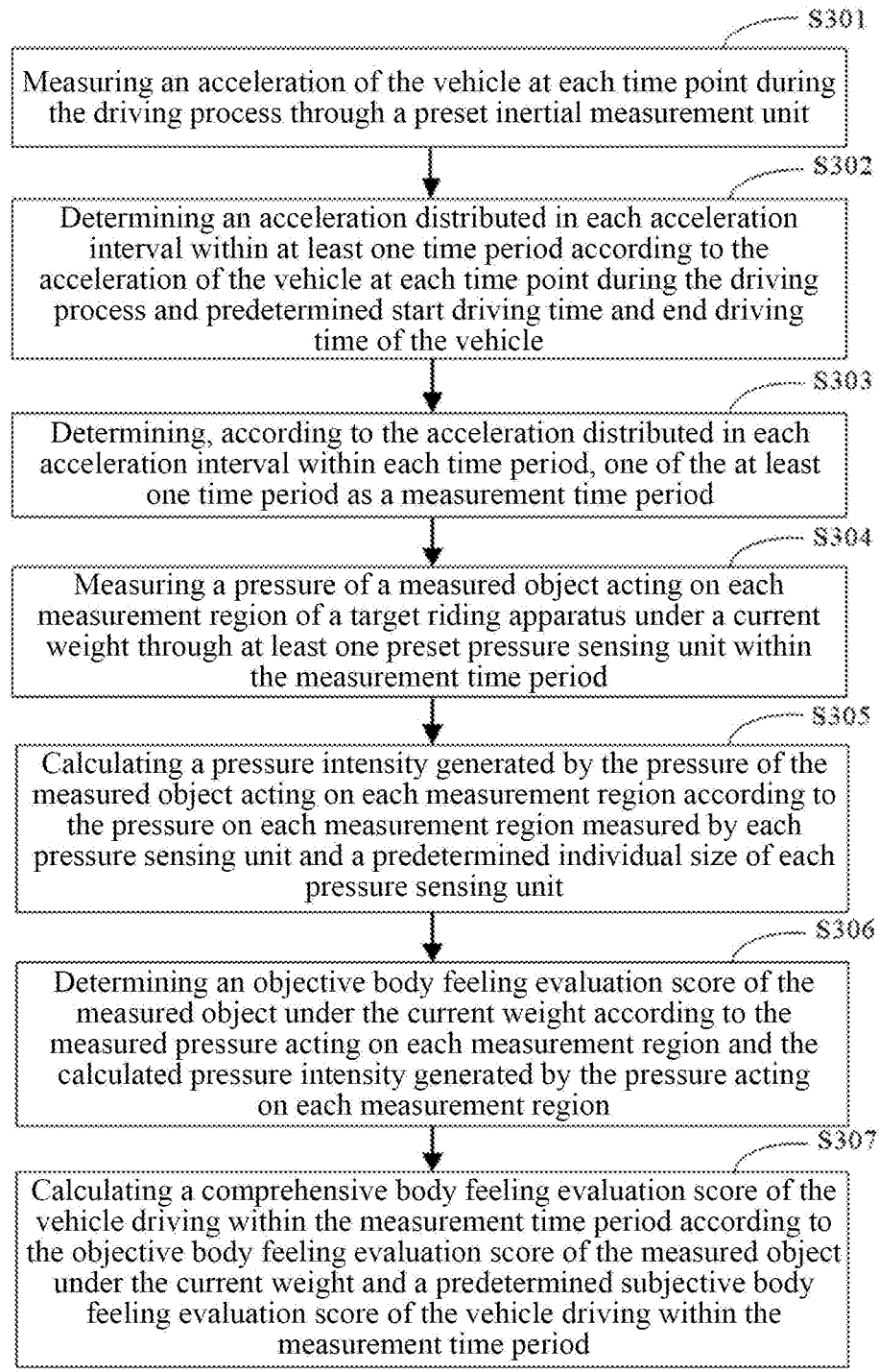
FIG. 3 is a schematic flowchart of a method for evaluating a body feeling of a vehicle according to a second embodiment of the present disclosure.

FIG. 3 is a schematic flowchart of a method for evaluating a body feeling of a vehicle according to the second embodiment of the present disclosure. The above technical solution is further optimized and expanded, and this embodiment may be combined with the above various optional implementations. As shown in FIG. 3, a method for evaluating a body feeling of a vehicle may include the following steps.

S301: measuring an acceleration of the vehicle at each time point during the driving process through a preset inertial measurement unit.

In this step, during the driving process of the vehicle, the electronic device may measure the acceleration of the vehicle at each time point during the driving process through the preset inertial measurement unit. The inertial measurement unit (IMU) is an apparatus that measures a three-axis attitude angle (or angular velocity) of an object and the acceleration. Generally, the IMU includes three single-axis accelerometers and three single-axis gyroscopes, the accelerometers detect acceleration signals of the object on three independent axes of a coordinate system of a carrier, while the gyroscopes detect angular velocity signals of the carrier relative to a navigation coordinate system, measure the angular velocity and acceleration of the object in a three-dimensional space, and calculate the attitude of the object.

S302: determining an acceleration distributed in each acceleration interval within at least one time period according to the acceleration of the vehicle at each time point during the driving process and predetermined start driving time and end driving time of the vehicle.

In this step, the electronic device may determine the acceleration distributed in each acceleration interval within at least one time period according to the acceleration of the vehicle at each time point during the driving process and the predetermined start driving time and end driving time of the vehicle. Specifically, the electronic device may divide the driving period of the vehicle from the start driving time to the end driving time into a plurality of time periods according to the predetermined start driving time and end driving time of the vehicle; then, assign the acceleration of the vehicle at each time point during the driving process into the corresponding time period; and determine the acceleration distributed in each acceleration interval within each time period according to the acceleration within each time period; where the number of the acceleration intervals and the boundary value of each interval may be predefined. For example, the acceleration intervals may include: a first interval, a second interval, and a third interval; where the first interval is 0-2 m/s$^2$; the second interval is 2-4 m/s$^2$; and the third interval is 4-6 m/s$^2$. The first interval having a small acceleration value can be referred to as a low-level interval; the second interval having a medium acceleration value can be referred to as a middle-level interval; and the third interval having a large acceleration value can be referred to as a high-level interval. The numbers of the low-level interval, the medium-level interval, and the high-level interval in embodiments of the present disclosure may be one or more. For example, assuming that the start driving time of the vehicle is 0:00, and the end driving time of the vehicle is 1:00; then, during the driving process of the vehicle, the driving period of 0:00-1:00 may be divided into a plurality of time periods. The number of the time periods may be determined according to the road conditions during the driving process of the vehicle; and the length of each time period may be the same or different. For example, the driving period of 0:00-1:00 may be divided into three time periods, respectively a first time period, a second time period, and a third time period; where, the first time period is 0:00-0:20; the second time period is 0:20-0:40; the third time period is 0:40-1:00; then, the acceleration at each time point may be assigned into the corresponding time period; and the acceleration distributed in each acceleration interval within each time period is determined according to the acceleration within each time period.

S303: determining, according to the acceleration distributed in each acceleration interval within each time period, one of the at least one time period as a measurement time period.

In this step, the electronic device may determine, according to the acceleration distributed in each acceleration interval within each time period, one of the at least one time period as a measurement time period. For example, when a plurality of accelerations are distributed in one or more high-level acceleration intervals, it indicates that the vehicle does not drive steadily within this time period, so this time period may be excluded when determining the measurement time period. Specifically, during the driving process of the vehicle, the acceleration is prone to drastic change when the vehicle passes through uneven regions. Therefore, when determining the measurement time period, the time period during which the acceleration changes drastically should be excluded.

S304: measuring a pressure of a measured object acting on each measurement region of a target riding apparatus under a current weight through at least one preset pressure sensing unit within the measurement time period.

S305: calculating a pressure intensity generated by the pressure of the measured object acting on each measurement region according to the pressure on each measurement region measured by each pressure sensing unit and a predetermined individual size of each pressure sensing unit.

S306: determining an objective body feeling evaluation score of the measured object under the current weight according to the measured pressure acting on each measurement region and the calculated pressure intensity generated by the pressure acting on each measurement region.

S307: calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period.

In the method for evaluating a body feeling of a vehicle according to embodiments of the present disclosure, a pressure of a measured object acting on each measurement region of a target riding apparatus under a current weight is first measured by at least one pressure sensing unit within a measurement time period; then, a pressure intensity generated by the pressure of the measured object acting on each measurement region is calculated according to the pressure on each measurement region measured by each pressure sensing unit and a predetermined individual size of each pressure sensing unit; next, an objective body feeling evaluation score of the measured object under the current weight is determined according to the measured pressure acting on each measurement region and the calculated pressure intensity generated by the pressure acting on each measurement region; and finally, a comprehensive body feeling evaluation score of the vehicle driving within the measurement time period is calculated according to the objective body feeling evaluation score of the measured object under the current weight and a predetermined subjective body feeling evaluation score of the vehicle driving within the measurement time period. That is to say, embodiments of the present disclosure may determine the objective body feeling evaluation score of the measured object under the current weight by means of measuring pressure values through the pressure sensing units, and the score does not rely on the subjective feeling of the passenger and can relatively objectively evaluate the riding experience of the vehicle. The existing method for evaluating a body feeling of a vehicle is mainly based on a method of subjective evaluation, so the evaluation result is subjectively affected. Because embodiments of the present disclosure use the technical means of measuring the pressure on each measurement region through at least one pressure sensing unit during the driving process of the vehicle, the technical problems in the existing technology that the body feeling evaluation is inaccurate and difficult to quantify are overcome. The technical solution provided in embodiments of the present disclosure can improve the accuracy of body feeling evaluation, reduce the one-sidedness of subjective evaluation, and obtain the quantified result of the body feeling measurement. In addition, the technical solution of embodiments of the embodiment of the present disclosure is simple and convenient to implement and easy to popularize, and has a wider application range.

Third Embodiment

Figure 4:
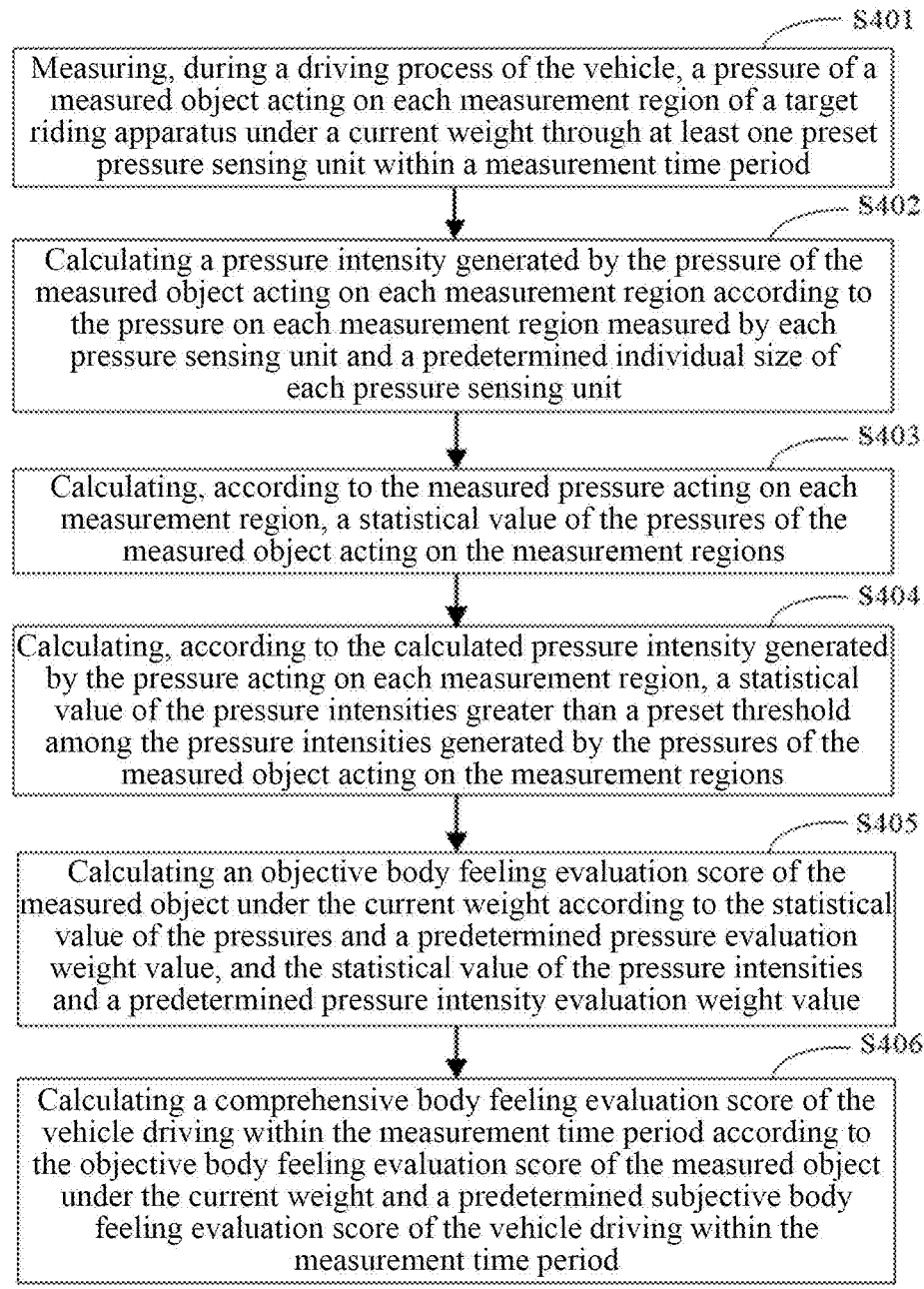
FIG. 4 is a schematic flowchart of a method for evaluating a body feeling of a vehicle according to a third embodiment of the present disclosure.

FIG. 4 is a schematic flowchart of a method for evaluating a body feeling of a vehicle according to the third embodiment of the present disclosure. The above technical solution is further optimized and expanded, and this embodiment can be combined with the above various optional implementations. As shown in FIG. 4, a method for evaluating a body feeling of a vehicle may include the following steps.

S401: measuring, during a driving process of the vehicle, a pressure of a measured object acting on each measurement region of a target riding apparatus under a current weight through at least one preset pressure sensing unit within a measurement time period.

S402: calculating a pressure intensity generated by the pressure of the measured object acting on each measurement region according to the pressure on each measurement region measured by each pressure sensing unit and a predetermined individual size of each pressure sensing unit.

S403: calculating, according to the measured pressure acting on each measurement region, a statistical value of the pressures of the measured object acting on the measurement regions.

In this step, the electronic device may calculate the statistical value of the pressures of the measured object acting on the measurement regions according to the measured pressure acting on each measurement region. Specifically, the electronic device may first obtain a maximum value and a minimum value of the pressure acting on each measurement region measured by each pressure sensing unit within the measurement time period; and then calculate an average value of the pressures acting on the measurement regions measured by the at least one pressure sensing unit within the measurement time period according to the maximum value and the minimum value of the pressure acting on each measurement region measured by each pressure sensing unit within the measurement time period and a predetermined number of the at least one pressure sensing unit. Specifically, the average value of the pressures acting on the measurement regions measured by the at least one pressure sensing unit within the measurement time period is determined by the following equation:

$$E_1 = \frac{1}{n}\left(\sum_{i=1}^{n}(x_{i\_max} R - x_{i\_max})\right);$$

where $E_1$ represents the average value of the pressures acting on the measurement regions measured by the at least one pressure sensing unit within the measurement time period; n represents the number of the at least one pressure sensing unit; i represents an order of a current pressure sensing unit in the at least one pressure sensing unit; $x_{i\_max}$ represents the maximum value of the pressure acting on the corresponding measurement region measured by the $i^{th}$ pressure sensing unit within the measurement time period; and $x_{i\_min}$ represents the minimum value of the pressure acting on the corresponding measurement region measured by the $i^{th}$ pressure sensing unit within the measurement time period.

S404: calculating, according to the calculated pressure intensity generated by the pressure acting on each measurement region, a statistical value of the pressure intensities greater than a preset threshold among the pressure intensities generated by the pressures of the measured object acting on the measurement regions.

In this step, the electronic device may calculate, according to the calculated pressure intensity generated by the pressure acting on each measurement region, the statistical value of the pressure intensities greater than the preset threshold among the pressure intensities generated by the pressures of the measured object acting on the measurement regions. Specifically, the electronic device may first extract the pressure intensities greater than the preset threshold from the calculated pressure intensities generated by the pressures acting on the measurement regions, and count a number of the pressure intensities greater than the preset threshold; and then calculate an average value of the pressure intensities greater than the preset threshold among the pressure intensities generated by the pressures of the measured object acting on the measurement regions according to the pressure intensities greater than the preset threshold, the number of the pressure intensities greater than the preset threshold, and the predetermined number of the at least one pressure sensing unit. Alternatively, the preset threshold in the present disclosure may be 12 KPa. Specifically, the average value of the pressure intensities greater than the preset threshold among the pressure intensities generated by the pressures of the measured object acting on the measurement regions is determined by the following equation:

$$E_2 = \frac{1}{n}\sum_{j=1}^{m} x_j;$$

where, $E_2$ represents the average value of the pressure intensities greater than the preset threshold among the pressure intensities generated by the pressures of the measured object acting on the measurement regions; n represents the number of the at least one pressure sensing unit; j represents the order of the current pressure sensing unit in the pressure sensing units that have measured the pressure intensities greater than the preset threshold; and $x_j$ represents the pressure intensity greater than the preset threshold measured by the $j^{th}$ pressure sensing unit within the measurement time period.

S405: calculating an objective body feeling evaluation score of the measured object under the current weight according to the statistical value of the pressures and a predetermined pressure evaluation weight value, and the statistical value of the pressure intensities and a predetermined pressure intensity evaluation weight value.

S406: calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period.

Figure 5:
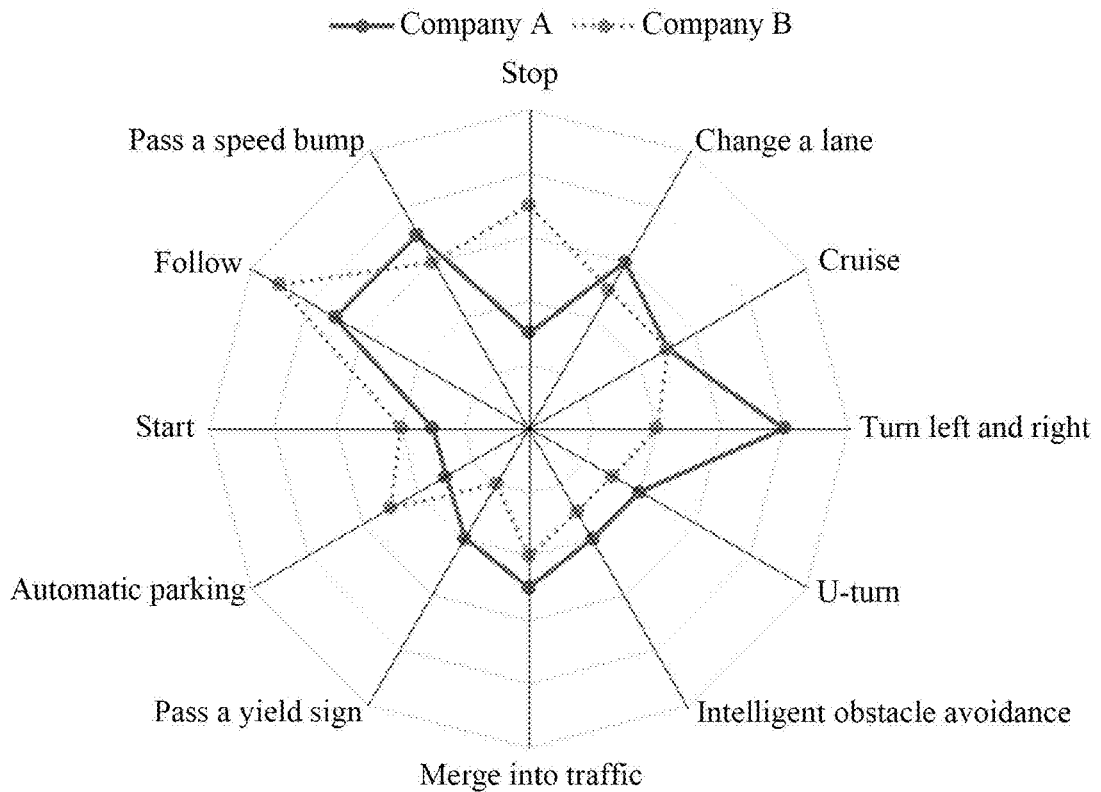
FIG. 5 is a schematic diagram of distribution of subjective body feeling evaluation scores according to the third embodiment of the present disclosure.

In a specific embodiment of the present disclosure, for each specific scenario of each driving behavior, the same subjective scoring standard may be used to subjectively evaluate the comfort. According to the ANSI/SAE J1441 standard, scores 1-4 indicate that the body feeling is unacceptable, and the functions related to the body feeling of the autonomous vehicle need to be redesigned; scores 5-6 indicate that the body feeling is acceptable, but there is room for further improvement; and score 7 and above indicate that there is no problem or very few problems with the body feeling, and the body feeling has reached the body feeling requirement of the passenger for the autonomous vehicle. Specifically, the subjective body feeling evaluation scores and the corresponding meanings and explanations of the scores may be shown in Table 2 below:

scenario is weighted to obtain a comprehensive subjective body feeling evaluation score. After the evaluation, the overall autonomous driving comfort can be evaluated by means of a radar map shown in FIG. 5, which can reflect the comfort level of the current vehicle and can also visually show the weak links of the current vehicle. As shown in FIG. 5, the schematic diagram of distribution includes five closed-loop curves, which may be marked from inside to outside as follows: curve 1, curve 2, curve 3, curve 4, and curve 5; among them, curve 1 represents a subjective body feeling evaluation score 2; curve 2 represents a subjective body feeling evaluation score 4; curve 3 represents a subjective body feeling evaluation score 6; curve 4 represents a subjective body feeling evaluation score 8; and curve 5 represents a subjective body feeling evaluation score 10. For a vehicle produced by company A and a vehicle produced by company B, subjective body feelings may be respectively evaluated for the specific scenarios of start, follow, passing a speed bump, stop, lane change, cruise, left and right turn, U-turn, intelligent obstacle avoidance, merging into traffic, passing a yield sign, and automatic parking, to obtain subjective body feeling evaluation scores under the specific scenarios. The subjective body feeling evaluation scores of the vehicle produced by company A are connected by a solid line; the subjective body feeling evaluation scores of the vehicle produced by company B are connected by a dotted line. Therefore, FIG. 5 can reflect the comfort levels of the vehicles produced by company A and company B, and can also visually show the weak links of each vehicle.

In the method for evaluating a body feeling of a vehicle according to embodiments of the present disclosure, a pressure of a measured object acting on each measurement region of a target riding apparatus under a current weight is first measured by at least one pressure sensing unit within a measurement time period; then, a pressure intensity generated by the pressure of the measured object acting on each measurement region is calculated according to the pressure on each measurement region measured by each pressure sensing unit and an individual size of each pressure sensing unit; next, an objective body feeling evaluation score of the measured object under the current weight is determined according to the measured pressure acting on each measurement region and the calculated pressure intensity generated by the pressure acting on each measurement region; and finally, a comprehensive body feeling evaluation score of the vehicle driving within the measurement time period is calculated according to the objective body feeling evaluation score of the measured object under the current weight and a predetermined subjective body feeling evaluation score of

TABLE 2

| Score | 1 | 2 | 3 | 4 | 5 | 6 | 7 | 8 | 9 | 10 |
|---|---|---|---|---|---|---|---|---|---|---|
| Meaning | Very bad | Bad | Relatively bad | Slightly bad | Acceptable | Qualified | Good | Very good | Excellent | Perfect |
| Explain | | Refuse to accept, redesign | | | Acceptable, further improvement | | No problem or very few problems | | | |

FIG. 5 is a schematic diagram of distribution of subjective body feeling evaluation scores according to the third embodiment of the present disclosure. For the 12 driving behaviors in Table 1 that are more likely to cause body feeling discomfort, a subjective body feeling may be evaluated for each specific scenario in each driving behavior, and then the body feeling evaluation score in each specific the vehicle driving within the measurement time period. That is to say, embodiments of the present disclosure may determine the objective body feeling evaluation score of the measured object under the current weight by means of measuring pressure values through the pressure sensing units, and the score does not rely on the subjective feeling of the passenger and can relatively objectively evaluate the riding experience of the vehicle. The existing method for evaluating a body feeling of a vehicle is mainly based on a method of subjective evaluation, so the evaluation result is subjectively affected. Because embodiments of the present disclosure use the technical means of measuring the pressure on each measurement region through at least one pressure sensing unit during the driving process of the vehicle, the technical problems in the existing technology that the body feeling evaluation is inaccurate and difficult to quantify are overcome. The technical solution provided in embodiments of the present disclosure can improve the accuracy of body feeling evaluation, reduce the one-sidedness of subjective evaluation, and obtain the quantified result of the body feeling measurement. In addition, the technical solution of embodiments of the present disclosure is simple and convenient to implement and easy to popularize, and has a wider application range.

Fourth Embodiment

Figure 6:
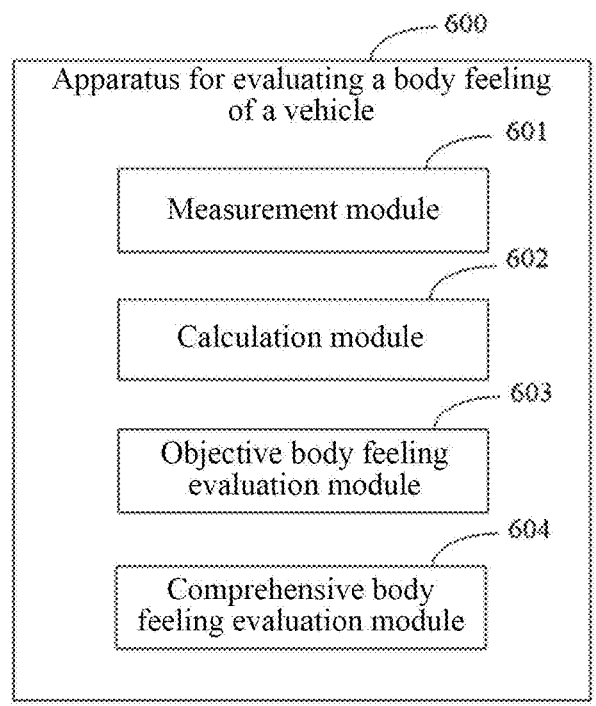
FIG. 6 is a schematic structural diagram of an apparatus for evaluating a body feeling of a vehicle according to a fourth embodiment of the present disclosure.

FIG. 6 is a schematic structural diagram of an apparatus for evaluating a body feeling of a vehicle according to the fourth embodiment of the present disclosure. As shown in FIG. 6, the apparatus 600 includes: a measurement module 601, a calculation module 602, an objective body feeling evaluation module 603, and a comprehensive body feeling evaluation module 604.

The measurement module 601 is configured to measure, during a driving process of the vehicle, a pressure of a measured object acting on each measurement region of a target riding apparatus under a current weight through at least one preset pressure sensing unit within a measurement time period.

The calculation module 602 is configured to calculate a pressure intensity generated by the pressure of the measured object acting on each measurement region according to the pressure on each measurement region measured by each pressure sensing unit and a predetermined individual size of each pressure sensing unit.

The objective body feeling evaluation module 603 is configured to determine an objective body feeling evaluation score of the measured object under the current weight according to the measured pressure acting on each measurement region and the calculated pressure intensity generated by the pressure acting on each measurement region.

The comprehensive body feeling evaluation module 604 is configured to calculate a comprehensive body feeling evaluation score of the vehicle driving within the measurement time period according to the objective body feeling evaluation score of the measured object under the current weight and a predetermined subjective body feeling evaluation score of the vehicle driving within the measurement time period.

Further, the objective body feeling evaluation module 603 is specifically configured to calculate, according to the measured pressure acting on each measurement region, a statistical value of the pressures of the measured object acting on the measurement regions; calculate, according to the calculated pressure intensity generated by the pressure acting on each measurement region, a statistical value of the pressure intensities greater than a preset threshold among the pressure intensities generated by the pressures of the measured object acting on the measurement regions; and calculate the objective body feeling evaluation score of the measured object under the current weight according to the statistical value of the pressures and a predetermined pressure evaluation weight value, and the statistical value of the pressure intensities and a predetermined pressure intensity evaluation weight value.

Further, the objective body feeling evaluation module 603 is specifically configured to obtain a maximum value and a minimum value of the pressure acting on each measurement region measured by each pressure sensing unit within the measurement time period; and calculate an average value of the pressures acting on the measurement regions measured by the at least one pressure sensing unit within the measurement time period according to the maximum value and the minimum value of the pressures acting on each measurement region measured by each pressure sensing unit within the measurement time period and a predetermined number of the at least one pressure sensing unit.

Further, the average value of the pressures acting on the measurement regions measured by the at least one pressure sensing unit within the measurement time period is determined by following equation:

$$E_1 = \frac{1}{n}\left(\sum_{i=1}^{n}(x_{i\_max} R - x_{i\_min})\right);$$

where $E_1$ represents the average value of the pressures acting on the measurement regions measured by the at least one pressure sensing unit within the measurement time period; n represents the number of the at least one pressure sensing unit; i represents an order of a current pressure sensing unit in the at least one pressure sensing unit; $x_{i\_max}$ represents the maximum value of the pressure acting on the corresponding measurement region a min measured by the $i^{th}$ pressure sensing unit within the measurement time period; and $x_{i\_min}$ represents the minimum value of the pressure acting on the corresponding measurement region measured by the $i^{th}$ pressure sensing unit within the measurement time period.

Further, the objective body feeling evaluation module 603 is specifically configured to extract the pressure intensities greater than the preset threshold from the calculated pressure intensities generated by the pressures acting on the measurement regions, and count a number of the pressure intensities greater than the preset threshold; and calculate an average value of the pressure intensities greater than the preset threshold among the pressure intensities generated by the pressures of the measured object acting on the measurement regions according to the pressure intensities greater than the preset threshold, the number of the pressure intensities greater than the preset threshold, and a predetermined number of the at least one pressure sensing unit.

Further, the average value of the pressure intensities greater than the preset threshold among the pressure intensities generated by the pressures of the measured object acting on the measurement regions is determined by following equation:

$$E_2 = \frac{1}{n}\sum_{j=1}^{m}x_j;$$

wherein $E_2$ represents the average value of the pressure intensities greater than the preset threshold among the pressure intensities generated by the pressures of the measured object acting on the measurement regions; n represents the number of the at least one pressure sensing unit; represents an order of a current pressure sensing unit in the pressure sensing units that have measured the pressure intensities greater than the preset threshold; and $x_j$ represents the pressure intensity greater than the preset threshold measured by the $i^{th}$ pressure sensing unit within the measurement time period.

Further, the apparatus further includes: a determination module 605 (not shown in the figure).

The measurement module 601 is further configured to measure an acceleration of the vehicle at each time point during the driving process through a preset inertial measurement unit.

The determination module 605 is configured to determine an acceleration distributed in each acceleration interval within at least one time period according to the acceleration of the vehicle at each time point during the driving process and predetermined start driving time and end driving time of the vehicle; and determine, according to the acceleration distributed in each acceleration interval within each time period, one of the at least one time period as the measurement time period.

The above-mentioned apparatus for evaluating a body feeling of a vehicle may execute the method provided in any embodiment of the present disclosure, and has corresponding functional modules for executing the method and corresponding beneficial effects. For technical details not described in this embodiment, reference may be made to the method for evaluating a body feeling of a vehicle according to any embodiment of the present disclosure.

Fifth Embodiment

According to embodiments of the present disclosure, the present disclosure further provides an electronic device and a readable storage medium.

Figure 7:
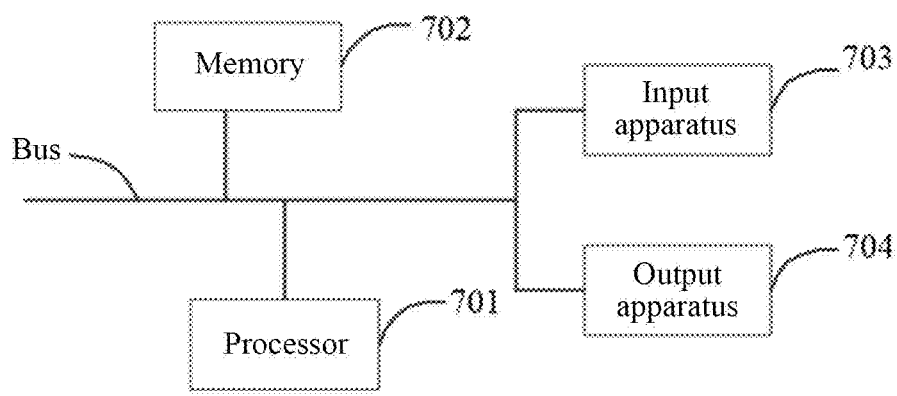
FIG. 7 is a block diagram of an electronic device for implementing the method for evaluating a body feeling of a vehicle according to embodiments of the present disclosure.

As shown in FIG. 7, FIG. 7 is a block diagram of an electronic device for implementing the method for evaluating a body feeling of a vehicle according to embodiments of the present disclosure. The electronic device is intended to represent various forms of digital computers, such as a laptop computer, a desktop computer, a workstation, a personal digital assistant, a server, a blade server, a mainframe computer, and other suitable computers. The electronic device may also represent various forms of mobile apparatuses, such as a personal digital processor, a cellular phone, a smart phone, a wearable device, and other similar computing apparatuses. The components, their connections and relationships, and their functions shown herein are merely examples, and are not intended to limit the implementation of embodiments of the present disclosure described and/or required herein. Typically, the electronic device disclosed in this embodiment may be used to exemplify the general structure of devices such as a vehicle, a mobile terminal, and a vehicle-mounted device.

As shown in FIG. 7, the electronic device includes: one or more processors 701, a memory 702, and interfaces for connecting various components, including high-speed interfaces and low-speed interfaces. The various components are connected to each other by different buses, and can be installed on a common mainboard or installed in other ways as required. The processor may process instructions executed in the electronic device, including instructions stored in or on the memory to display graphical information of a graphical user interface (GUI) on an external input/output apparatus (such as a display device coupled to an interface). In other embodiments, a plurality of processors and/or a plurality of buses may be used with a plurality of memories if necessary. Similarly, a plurality of electronic devices may be connected, and each device provides some necessary operations, for example, as a server array, a group of blade servers, or a multi-processor system. One processor 701 is taken as an example in FIG. 7.

The memory 702 is a non-transitory computer readable storage medium according to an embodiment of the present disclosure. The memory stores instructions executable by at least one processor, causing the at least one processor to execute the method for evaluating a body feeling of a vehicle according to embodiments of the present disclosure. The non-transitory computer readable storage medium according to embodiments of the present disclosure stores computer instructions, and the computer instructions are used for a computer to execute the method for evaluating a body feeling of a vehicle according to embodiments of the present disclosure.

As a non-transitory computer readable storage medium, the memory 702 may be used to store non-transitory software programs, non-transitory computer-executable programs, and modules, such as program instructions/modules corresponding to the method for evaluating a body feeling of a vehicle according to embodiments of the present disclosure, for example, the measurement module 601, the calculation module 602, the objective body feeling evaluation module 603, and the comprehensive body feeling evaluation module 604 shown in FIG. 6. The processor 701 executes various functional applications and data processing of the electronic device by running the non-transitory software programs, instructions, and modules stored in the memory 702, that is, implements the method for evaluating a body feeling of a vehicle according to embodiments of the method.

The memory 702 may include a program storage area and a data storage area, where the program storage area may store an operating system and an application program required by at least one function; and the data storage area may store data created by the use of the electronic device according to the method for evaluating a body feeling of a vehicle. In addition, the memory 702 may include a high-speed random access memory, and may further include a non-transitory memory, such as at least one magnetic disk storage device, a flash memory device, or other non-transitory solid-state storage devices. In some embodiments, the memory 702 may optionally include memories remotely configured with respect to the processor 701, and these remote memories may be connected to the electronic device used to implement the method for evaluating a body feeling of a vehicle in embodiments of the present disclosure through a network. Examples of the network include, but are not limited to, the Internet, an intranet, a local area network, a mobile communications network, or a combination thereof.

The electronic device for implementing the method for evaluating a body feeling of a vehicle in embodiments of the present disclosure may further include: an input apparatus 703 and an output apparatus 704. The processor 701, the memory 702, the input apparatus 703, and the output apparatus 704 may be connected by a bus or other means, exemplified by a bus in FIG. 7.

The input apparatus 703 may receive input digital or character information, and generate key signal inputs related to the user settings and function control of the electronic device used to implement the method for evaluating a body feeling of a vehicle in embodiments of the present disclosure, such as a touch screen, a keypad, a mouse, a trackpad, a touchpad, an indicating arm, one or more mouse buttons, a trackball, a joystick and other input apparatuses. The output apparatus 704 may include a display device, an auxiliary lighting apparatus and a tactile feedback apparatus, wherein the auxiliary lighting apparatus is, for example, a light emitting diode (LED); and the tactile feedback apparatus is, for example, a vibration motor. The display device may include, but is not limited to, a liquid crystal display (LCD), an LED display, and a plasma display. In some embodiments, the display device may be a touch screen.

Various implementations of the systems and techniques described herein may be implemented in a digital electronic circuit system, an integrated circuit system, an application specific integrated circuit (ASIC), computer hardware, firmware, software, and/or combinations thereof. These various implementations may include the implementation in one or more computer programs. The one or more computer programs may be executed and/or interpreted on a programmable system including at least one programmable processor, and the programmable processor may be a dedicated or general-purpose programmable processor, may receive data and instructions from a storage system, at least one input apparatus and at least one output apparatus, and transmit the data and the instructions to the storage system, the at least one input apparatus and the at least one output apparatus.

These computing programs, also referred to as programs, software, software applications or codes, include a machine instruction of the programmable processor, and may be implemented using a high-level procedural and/or an object-oriented programming language, and/or an assembly/machine language. As used herein, the terms "machine readable medium" and "computer readable medium" refer to any computer program product, device and/or apparatus (e.g., a magnetic disk, an optical disk, a storage device and a programmable logic device (PLD)) used to provide a machine instruction and/or data to the programmable processor, and include a machine readable medium that receives the machine instruction as a machine readable signal. The term "machine readable signal" refers to any signal used to provide the machine instruction and/or data to the programmable processor.

To provide an interaction with a user, the systems and techniques described here may be implemented on a computer having a display apparatus (e.g., a cathode ray tube (CRT) or an LCD monitor) for displaying information to the user, and a keyboard and a pointing apparatus (e.g., a mouse or a track ball) by which the user may provide the input to the computer. Other kinds of apparatuses may also be used to provide the interaction with the user. For example, a feedback provided to the user may be any form of sensory feedback (e.g., a visual feedback, an auditory feedback, or a tactile feedback); and an input from the user may be received in any form, including acoustic, speech, or tactile input.

The systems and techniques described here may be implemented in a computing system (e.g., as a data server) that includes a backend part, implemented in a computing system (e.g., an application server) that includes a middleware part, implemented in a computing system (e.g., a user computer having a graphical user interface or a Web browser through which the user may interact with an implementation of the systems and techniques described here) that includes a frontend part, or implemented in a computing system that includes any combination of the backend part, the middleware part or the frontend part. The parts of the system may be interconnected by any form or medium of digital data communication (e.g., a communication network). Examples of the communication network include a local area network (LAN), a wide area network (WAN) and Internet.

The computer system may include a client and a server. The client and the server are generally remote from each other and typically interact through the communication network. The relationship between the client and the server is generated through computer programs running on the respective computers and having a client-server relationship to each other.

According to the technical solution of embodiments of the present disclosure, a pressure of a measured object acting on each measurement region of a target riding apparatus under a current weight is first measured by at least one pressure sensing unit within a measurement time period; then, a pressure intensity generated by the pressure of the measured object acting on each measurement region is calculated according to the pressure on each measurement region measured by each pressure sensing unit and an individual size of each pressure sensing unit; next, an objective body feeling evaluation score of the measured object under the current weight is determined according to the measured pressure acting on each measurement region and the calculated pressure intensity generated by the pressure acting on each measurement region; and finally, a comprehensive body feeling evaluation score of the vehicle driving within the measurement time period is calculated according to the objective body feeling evaluation score of the measured object under the current weight and a predetermined subjective body feeling evaluation score of the vehicle driving within the measurement time period. That is to say, embodiments of the present disclosure may determine the objective body feeling evaluation score of the measured object under the current weight by means of measuring pressure values through the pressure sensing units, and the score does not rely on the subjective feeling of the passenger and can relatively objectively evaluate the riding experience of the vehicle. The existing method for evaluating a body feeling of a vehicle is mainly based on a method of subjective evaluation, so the evaluation result is subjectively affected. Because embodiments of the present disclosure use the technical means of measuring the pressure on each measurement region through at least one pressure sensing unit during the driving process of the vehicle, the technical problems in the existing technology that the body feeling evaluation is inaccurate and difficult to quantify are overcome. The technical solution provided in embodiments of the present disclosure can improve the accuracy of body feeling evaluation, reduce the one-sidedness of subjective evaluation, and obtain the quantified result of the body feeling measurement. In addition, the technical solution of embodiments of the present disclosure is simple and convenient to implement and easy to popularize, and has a wider application range.

It should be understood that the various forms of processes shown above can be used to reorder, add, or delete steps. For example, the steps disclosed in embodiments of the present disclosure can be executed in parallel, sequentially, or in different orders, as long as the desired results of the technical solutions disclosed in embodiments of the present disclosure can be achieved. This is not limited herein.

The above specific implementations do not constitute a limitation to the protection scope of the present disclosure. It should be understood by those skilled in the art that various modifications, combinations, sub-combinations, and replacements may be made according to the design requirements and other factors. Any modification, equivalent replacement, improvement, and the like made within the spirit and principle of the present disclosure should be included within the protection scope of the present disclosure.

What is claimed is:

1. A method for evaluating a body feeling of a vehicle, the method comprising:
   measuring, during a driving process of the vehicle, a pressure of a measured object acting on each measurement region of a target riding apparatus under a current weight through at least one pressure sensing unit within a measurement time period;
   calculating a pressure intensity generated by the pressure of the measured object acting on each measurement region according to the pressure on each measurement region measured by each pressure sensing unit and a predetermined individual size of each pressure sensing unit;
   determining an objective body feeling evaluation score of the measured object under the current weight according to the measured pressure acting on each measurement region and the calculated pressure intensity generated by the pressure acting on each measurement region;
   calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period;
   measuring an acceleration of the vehicle at each time point during the driving process through a preset inertial measurement unit;
   determining an acceleration distributed in each acceleration interval within at least one time period according to the acceleration of the vehicle at each time point during the driving process and predetermined start driving time and end driving time of the vehicle; and
   determining, according to the acceleration distributed in each acceleration interval within each time period, one of the at least one time period as the measurement time period.

2. The method according to claim 1, wherein the determining the objective body feeling evaluation score of the measured object under the current weight according to the measured pressure acting on each measurement region and the calculated pressure intensity generated by the pressure acting on each measurement region comprises:
   calculating, according to the measured pressure acting on each measurement region, a statistical value of the pressures of the measured object acting on the measurement regions;
   calculating, according to the calculated pressure intensity generated by the pressure acting on each measurement region, a statistical value of the pressure intensities greater than a preset threshold among the pressure intensities generated by the pressures of the measured object acting on the measurement regions; and
   calculating the objective body feeling evaluation score of the measured object under the current weight according to the statistical value of the pressures and a predetermined pressure evaluation weight value, and the statistical value of the pressure intensities and a predetermined pressure intensity evaluation weight value.

3. The method according to claim 2, wherein the calculating, according to the measured pressure acting on each measurement region, the statistical value of the pressures of the measured object acting on the measurement regions comprises:
   obtaining a maximum value and a minimum value of the pressure acting on each measurement region measured by each pressure sensing unit within the measurement time period; and
   calculating an average value of the pressures acting on the measurement regions measured by the at least one pressure sensing unit within the measurement time period according to the maximum value and the minimum value of the pressure acting on each measurement region measured by each pressure sensing unit within the measurement time period and a predetermined number of the at least one pressure sensing unit.

4. The method according to claim 3, wherein the average value of the pressures acting on the measurement regions measured by the at least one pressure sensing unit within the measurement time period is determined by following equation:

$$E_1 = \frac{1}{n}\left(\sum_{i=1}^{n}(x_{i\_max} R - x_{i\_min})\right)$$

wherein $E_1$ represents the average value of the pressures acting on the measurement regions measured by the at least one pressure sensing unit within the measurement time period; n represents the number of the at least one pressure sensing unit; i represents an order of a current pressure sensing unit in the at least one pressure sensing unit; $x_{i\_max}$ represents the maximum value of the pressure acting on a corresponding measurement region measured by $i^{th}$ pressure sensing unit within the measurement time period; and $x_{i\_min}$ represents the minimum value of the pressure acting on the corresponding measurement region measured by the $i^{th}$ pressure sensing unit within the measurement time period.

5. The method according to claim 2, wherein the calculating, according to the calculated pressure intensity generated by the pressure acting on each measurement region, the statistical value of the pressure intensities greater than the preset threshold among the pressure intensities generated by the pressures of the measured object acting on the measurement regions comprises:
   extracting the pressure intensities greater than the preset threshold from the calculated pressure intensities generated by the pressures acting on the measurement regions, and counting a number of the pressure intensities greater than the preset threshold; and
   calculating an average value of the pressure intensities greater than the preset threshold among the pressure intensities generated by the pressures of the measured object acting on the measurement regions according to the pressure intensities greater than the preset threshold, the number of the pressure intensities greater than the preset threshold, and a predetermined number of the at least one pressure sensing unit.

6. The method according to claim 5, wherein the average value of the pressure intensities greater than the preset threshold among the pressure intensities generated by the pressures of the measured object acting on the measurement regions is determined by following equation:

$$E_2 = \frac{1}{n}\sum_{j=1}^{m} X_j;$$

wherein $E_2$ represents the average value of the pressure intensities greater than the preset threshold among the pressure intensities generated by the pressures of the measured object acting on the measurement regions; n represents the number of the at least one pressure sensing unit; j represents an order of a current pressure sensing unit in the pressure sensing units that have measured the pressure intensities greater than the preset threshold; $x_j$ represents the pressure intensity greater than the preset threshold measured by $j^{th}$ pressure sensing unit within the measurement time period.

7. An electronic device, comprising:
at least one processor; and
a memory communicatively connected with the at least one processor;
the memory storing instructions executable by the at least one processor, and the instructions, when executed by the at least one processor, causing the at least one processor to perform operations, the operations comprising:
measuring, during a driving process of a vehicle, a pressure of a measured object acting on each measurement region of a target riding apparatus under a current weight through at least one pressure sensing unit within a measurement time period;
calculating a pressure intensity generated by the pressure of the measured object acting on each measurement region according to the pressure on each measurement region measured by each pressure sensing unit and a predetermined individual size of each pressure sensing unit;
determining an objective body feeling evaluation score of the measured object under the current weight according to the measured pressure acting on each measurement region and the calculated pressure intensity generated by the pressure acting on each measurement region;
calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period;
measuring an acceleration of the vehicle at each time point during the driving process through a preset inertial measurement unit;
determining an acceleration distributed in each acceleration interval within at least one time period according to the acceleration of the vehicle at each time point during the driving process and predetermined start driving time and end driving time of the vehicle; and
determining, according to the acceleration distributed in each acceleration interval within each time period, one of the at least one time period as the measurement time period.

8. The electronic device according to claim 7, wherein the determining the objective body feeling evaluation score of the measured object under the current weight according to the measured pressure acting on each measurement region and the calculated pressure intensity generated by the pressure acting on each measurement region comprises:
calculating, according to the measured pressure acting on each measurement region, a statistical value of the pressures of the measured object acting on the measurement regions;
calculating, according to the calculated pressure intensity generated by the pressure acting on each measurement region, a statistical value of the pressure intensities greater than a preset threshold among the pressure intensities generated by the pressures of the measured object acting on the measurement regions; and calculating the objective body feeling evaluation score of the measured object under the current weight according to the statistical value of the pressures and a predetermined pressure evaluation weight value, and the statistical value of the pressure intensities and a predetermined pressure intensity evaluation weight value.

9. The electronic device according to claim 8, wherein the calculating, according to the measured pressure acting on each measurement region, the statistical value of the pressures of the measured object acting on the measurement regions comprises:
obtaining a maximum value and a minimum value of the pressure acting on each measurement region measured by each pressure sensing unit within the measurement time period; and
calculating an average value of the pressures acting on the measurement regions measured by the at least one pressure sensing unit within the measurement time period according to the maximum value and the minimum value of the pressure acting on each measurement region measured by each pressure sensing unit within the measurement time period and a predetermined number of the at least one pressure sensing unit.

10. The electronic device according to claim 9, wherein the average value of the pressures acting on the measurement regions measured by the at least one pressure sensing unit within the measurement time period is determined by following equation:

$$E_1 = \frac{1}{n}\left(\sum_{i=1}^{n} (x_{i\_max} R - x_{i\_min})\right)$$

wherein $E_1$ represents the average value of the pressures acting on the measurement regions measured by the at least one pressure sensing unit within the measurement time period; n represents the number of the at least one pressure sensing unit; i represents an order of a current pressure sensing unit in the at least one pressure sensing unit; $x_{i\_max}$ represents the maximum value of the pressure acting on a corresponding measurement region measured by $i^{th}$ pressure sensing unit within the measurement time period; and $x_{i\_min}$ represents the minimum value of the pressure acting on the corresponding measurement region measured by the $i^{th}$ pressure sensing unit within the measurement time period.

11. The electronic device according to claim 8, wherein the calculating, according to the calculated pressure intensity generated by the pressure acting on each measurement region, the statistical value of the pressure intensities greater than the preset threshold among the pressure intensities generated by the pressures of the measured object acting on the measurement regions comprises:
extracting the pressure intensities greater than the preset threshold from the calculated pressure intensities generated by the pressures acting on the measurement regions, and counting a number of the pressure intensities greater than the preset threshold; and calculating an average value of the pressure intensities greater than the preset threshold among the pressure intensities generated by the pressures of the measured object acting on the measurement regions according to the pressure intensities greater than the preset threshold, the number of the pressure intensities greater than the preset threshold, and a predetermined number of the at least one pressure sensing unit.

12. The electronic device according to claim 11, wherein the average value of the pressure intensities greater than the preset threshold among the pressure intensities generated by the pressures of the measured object acting on the measurement regions is determined by following equation:

$$E_2 = \frac{1}{n}\sum_{j=1}^{m} x_j;$$

wherein $E_2$ represents the average value of the pressure intensities greater than the preset threshold among the pressure intensities generated by the pressures of the measured object acting on the measurement regions; n represents the number of the at least one pressure sensing unit; j represents an order of a current pressure sensing unit in the pressure sensing units that have measured the pressure intensities greater than the preset threshold; and $x_j$ represents the pressure intensity greater than the preset threshold measured by $j^{th}$ pressure sensing unit within the measurement time period.

13. A non-transitory computer readable storage medium storing computer instructions, the computer instructions, when executed by a computer, causing the computer to perform operations, the operations comprising:

measuring, during a driving process of a vehicle, a pressure of a measured object acting on each measurement region of a target riding apparatus under a current weight through at least one preset pressure sensing unit within a measurement time period;

calculating a pressure intensity generated by the pressure of the measured object acting on each measurement region according to the pressure on each measurement region measured by each pressure sensing unit and a predetermined individual size of each pressure sensing unit;

determining an objective body feeling evaluation score of the measured object under the current weight according to the measured pressure acting on each measurement region and the calculated pressure intensity generated by the pressure acting on each measurement region;

calculating a comprehensive body feeling evaluation score of the vehicle driving within the measurement time period according to the objective body feeling evaluation score of the measured object under the current weight and a predetermined subjective body feeling evaluation score of the vehicle driving within the measurement time period;

measuring an acceleration of the vehicle at each time point during the driving process through a preset inertial measurement unit;

determining an acceleration distributed in each acceleration interval within at least one time period according to the acceleration of the vehicle at each time point during the driving process and predetermined start driving time and end driving time of the vehicle; and determining, according to the acceleration distributed in each acceleration interval within each time period, one of the at least one time period as the measurement time period.

* * * * *

UNITED STATES PATENT AND TRADEMARK OFFICE
CERTIFICATE OF CORRECTION

PATENT NO. : 11,898,936 B2
APPLICATION NO. : 17/215628
DATED : February 13, 2024
INVENTOR(S) : Yiqun Fu et al.

It is certified that error appears in the above-identified patent and that said Letters Patent is hereby corrected as shown below:

In the Claims

Claim 4, in Column 20, Lines 23-26 (approximately), delete:

" $E_1 = \frac{1}{n}\left(\sum_{i=1}^{n}(x_{i\_max} R - x_{i\_min})\right)$ " and insert -- $E_1 = \frac{1}{n}(\sum_{i=1}^{n}(x_{i\_max} - x_{i\_min}))$ --

Claim 10, in Column 22, Lines 41-44 (approximately), delete:

" $E_1 = \frac{1}{n}\left(\sum_{i=1}^{n}(x_{i\_max} R - x_{i\_min})\right)$ " and insert -- $E_1 = \frac{1}{n}(\sum_{i=1}^{n}(x_{i\_max} - x_{i\_min}))$ --

Signed and Sealed this
Sixteenth Day of April, 2024

Katherine Kelly Vidal
*Director of the United States Patent and Trademark Office*